United States Patent [19]

Quinn et al.

[11] Patent Number: 5,750,329
[45] Date of Patent: *May 12, 1998

[54] METHODS AND COMPOSITIONS FOR AN ARTIFICIAL LUNG ORGAN CULTURE SYSTEM

[75] Inventors: Frederick D. Quinn, Decatur; Kristin A. Birkness, Atlanta, both of Ga.

[73] Assignee: Centers for Disease Control and Prevention, Atlanta, Ga.

[ * ] Notice: The term of this patent shall not extend beyond the expiration date of Pat. No. 5,695,996.

[21] Appl. No.: 679,081

[22] Filed: Jul. 12, 1996

Related U.S. Application Data

[63] Continuation-in-part of Ser. No. 311,762, Sep. 23, 1994.
[51] Int. Cl.$^6$ .............................. C12N 5/00; C12N 5/02; C12N 5/08; C12N 5/12
[52] U.S. Cl. .................. 435/1.1; 435/284.1; 435/287; 435/325; 435/347; 435/371; 435/373; 435/395
[58] Field of Search .................. 435/1.1, 284.1, 435/325, 287, 347, 371, 373, 395

[56] References Cited

U.S. PATENT DOCUMENTS 5,374,515  12/1994  Parenterau et al. ..................... 435/1

OTHER PUBLICATIONS

Mehta et al. "Comparison of In vivo Models for the Study of *Mycobacterium tuberculosis* Invasion and Intracellular Replication" *Infec. and Immun.* 64(7):2673–2679, Jul. 1996.
McDonough et al. "Pathogenesis of Tuberculosis: Interaction of *Mycobacterium tuberculosis* with Macrophages" *Infec. and Immun.* 61(7):2763–2773, Jul. 1993.
Graham et al. "Aortic Endothelial and Smooth Muscle Cell Co–Culture: An In vitro Model of the Arterial Wall" *J. Investigative Surgery* 4:487–494, 1991.
ATCC Catalogue of Cell Lines and Hybridomas 1992, 7th edition, pp. 4, 17, 100, 254 and 255, Jan. 1, 1992.
Shannon et al 1987 Biochem. et Biophys. Acta v 931 pp. 143–156.

*Primary Examiner*—Marian C. Knode
*Assistant Examiner*—Mary K. Zeman
*Attorney, Agent, or Firm*—Jones & Askew, LLP

[57] ABSTRACT

The present invention provides an artificial organ system comprising an endothelial cell layer, an epithelial cell layer and an artificial microporous membrane, having pores therein, disposed between and in direct contact with the endothelial cell layer and the epithelial cell layer such that the membrane has an endothelial side and an epithelial side. The present invention also provides an artificial organ system contained in a vessel comprising an upper chamber into which the epithelial side faces and containing the epithelial cell layer, and a lower chamber into which the endothelial side faces and containing the endothelial cells. The present invention also provides an artificial lung system comprising an endothelial cell layer, an alveolar epithelial cell layer and an artificial microporous membrane, having pores therein, disposed between and in direct contact with the endothelial cell layer and the alveolar epithelial cell layer such that the membrane has an endothelial side and an epithelial side. A method is also provided for constructing an artificial lung system, comprising placing an artificial microporous membrane, having pores therein, into a vessel having a bottom and supporting the membrane a distance from the bottom of the vessel to create an upper and lower chamber in the vessel such that the membrane has an endothelial side facing into the lower chamber of the vessel and an opposite epithelial side facing into the upper chamber of the vessel; placing endothelial cells into the upper chamber of the vessel under conditions such that the endothelial cells form a confluent layer of cells on the epithelial side of the membrane; and placing alveolar epithelial cells into the upper chamber of the vessel under conditions such that the endothelial cells migrate through the pores in the membrane and attach to the endothelial side of the membrane to form a confluent layer of the endothelial cells on the endothelial side of the membrane in the lower chamber and the alveolar epithelial cells form a confluent layer of the epithelial cells on the epithelial side of the membrane in the upper chamber.

24 Claims, No Drawings

METHODS AND COMPOSITIONS FOR AN ARTIFICIAL LUNG ORGAN CULTURE SYSTEM

This application is a continuation-in-part of application Ser. No. 08/311,762, filed Sep. 23, 1994, which is pending.

BACKGROUND OF THE INVENTION

1. Field of the Invention

The present invention relates to an artificial organ culture system comprising an endothelial cell layer and an epithelial cell layer oriented on either side of and in direct contact with an artificial microporous membrane. In addition, the present invention relates to an artificial lung organ culture system comprising an endothelial cell layer and an alveolar epithelial cell layer oriented on either side of and in direct contact with an artificial microporous membrane. The present invention also relates to methods for constructing an artificial organ culture system and for studying the passage of pathogens and chemical substances through the artificial organ culture system. The present invention further relates to methods for constructing an artificial lung organ culture system and for studying the passage of pathogens and chemical substances through the artificial organ culture system.

2. Background Art

The recent resurgence of tuberculosis in all parts of the world has brought new focus to the study of its pathogenesis. Worldwide, *Mycobacterium tuberculosis* infects two billion people and causes three million deaths each year. Re-emergence of tuberculosis in the United States with a marked increase in the incidence of multidrug resistant strains is in part due to increases in acquired or re-activated disease in individuals infected with human immunodeficiency virus (HIV). The search for improved methods of prevention and control requires a better understanding of the pathogenic mechanisms of this organism.

*Mycobacterium tuberculosis* is inhaled into the lung, eventually reaching the alveoli where the organism is ingested by alveolar macrophages. It is suspected that, if not killed by the macrophages, the bacillus is able to survive, replicate intracellularly and spread to other alveolar macrophages and to the nonactivated bloodborne macrophages attracted to the infection site by the released bacterial cell debris and host chemotactic factors (1). It is the dissemination of viable organisms into the lymph or circulatory system that is critical to the establishment of infection (2,3).

In vitro studies using cultured pneumocyte monolayers have shown that *Mycobacterium tuberculosis* bacilli were able not only to enter these cells but also to multiply intracellularly in far greater numbers than those seen within cultured macrophages. Similar studies have also shown intracellular growth within cultured human lung endothelial cells (4). Thus, even a few organisms inhaled into the alveolar space could potentially multiply to a much larger number before passing through the epithelial cells lining the alveolar spaces and into the blood stream.

Current knowledge of the pathogenesis of *Mycobacterium tuberculosis* is based on studies using animal models or in vitro studies using tissue culture monolayers. The fact that many of these animal models do not develop mycobacterial disease limits their relevance to the study of the human disease process. Even in animals susceptible to mycobacterial infection, the immune response is not the same as human response to the same infection. Human tissue culture cell monolayers are simpler to work with, can be maintained under controlled conditions and are more relevant to human disease. However, when infecting a human host, the bacillus must interact with more than a monolayer of cells. Thus, there exists a need for a model that is easy to work with, but also incorporates the added complexity of the cell-to-cell communication associated with multiple layers and allows for interactions with components of the immune response elicited by the presence of foreign substances.

The present invention meets this need by providing an artificial organ system incorporating epithelial and endothelial cell layers on a microporous membrane to examine the process of attachment and passage that occur as a pathogen or foreign substance makes its way from the mucosal surface, through the epithelial cells and into the vascular system. In addition, the present invention provides an artificial lung system incorporating endothelial and alveolar epithelial cell layers on a microporous membrane to examine the process of attachment and passage that occur as a pulmonary pathogen or foreign substance makes its way from the alveolar surface, through the epithelial cells and into the vascular system.

The present invention was created fortuitously and unexpectedly. The inventors were originally attempting to culture a layer of epithelial cells directly on top of a layer of endothelial cells. Previous attempts to accomplish this had resulted in the epithelial cells outgrowing the endothelial cells (5). The inventors attempted to overcome the overgrowth problem by first establishing a layer of endothelial cells on an artificial microporous membrane suspended in a tissue culture well in the hope that nutrients in the fluid medium would remain accessible to the endothelial cells even after the epithelial cell layer was established on top of the endothelial cell layer. It was reasoned that greater exposure to nutrients might prevent the underlying endothelial cell layer from being starved and killed by the epithelial cells. Quite unexpectedly, upon addition of epithelial cells to the layer of endothelial cells growing on the membrane, the endothelial cells migrated through the pores of the membrane and grew into a layer of cells on the opposite side of the membrane, effectively establishing stable layers of two different cell types in very close proximity to one another.

This organization of cells allows the two different cell types to communicate and interact as they might in vivo. The system is easier to obtain and to use than any of the animal models and by making use of human cells, is more relevant to the pathogenesis of an exclusively human disease. The present system is consistently reproducible without the variability inherent in animal models and human monolayer cultures. The system can be maintained without the use of antibiotics and remains both viable and usable for a longer period of time than other systems.

The present artificial lung system is a useful model for the study of the attachment and invasion factors contributing to *Mycobacterium tuberculosis* pathogenesis and lends itself to similar studies with other pathogens. Also, mutants and epidemic and sporadic case and carrier strains can be examined as they pass through the artificial lung system to determine which genes are turned on or off in response to changes in the environment and changes in the requirements for bacterial survival.

SUMMARY OF THE INVENTION

The present invention provides an artificial organ system comprising an endothelial cell layer, an epithelial cell layer and an artificial microporous membrane, having pores therein, disposed between and in direct contact with the endothelial cell layer and the epithelial cell layer such that the membrane has an endothelial side and an epithelial side. The present invention also provides an artificial organ system contained in a vessel comprising an upper chamber into which the epithelial side faces and containing the epithelial cell layer, and a lower chamber into which the endothelial side faces and containing the endothelial cells.

The present invention also provides an artificial lung system comprising an endothelial cell layer, an alveolar epithelial cell layer and an artificial microporous membrane, having pores therein, disposed between and in direct contact with the endothelial cell layer and the alveolar epithelial cell layer such that the membrane has an endothelial side and an epithelial side. The present invention also provides an artificial lung system contained in a vessel comprising an upper chamber into which the epithelial side faces and containing the alveolar epithelial cell layer, and a lower chamber into which the endothelial side faces and containing the endothelial cells.

Also provided is a method of constructing an artificial organ system, comprising placing an artificial microporous membrane, having pores therein, into a vessel having a bottom and supporting the membrane a distance from the bottom of the vessel to create an upper and lower chamber in the vessel such that the membrane has an endothelial side facing into the lower chamber of the vessel and an opposite epithelial side facing into the upper chamber of the vessel; placing endothelial cells into the upper chamber of the vessel under conditions such that the endothelial cells form a confluent layer of cells on the epithelial side of the membrane; and placing epithelial cells into the upper chamber of the vessel under conditions such that the endothelial cells migrate through the pores in the membrane and attach to the endothelial side of the membrane to form a confluent layer of the endothelial cells on the endothelial side of the membrane in the lower chamber and the epithelial cells form a confluent layer of the epithelial cells on the epithelial side of the membrane in the upper chamber.

A method is also provided for constructing an artificial lung system, comprising placing an artificial microporous membrane, having pores therein, into a vessel having a bottom and supporting the membrane a distance from the bottom of the vessel to create an upper and lower chamber in the vessel such that the membrane has an endothelial side facing into the lower chamber of the vessel and an opposite epithelial side facing into the upper chamber of the vessel; placing endothelial cells into the upper chamber of the vessel under conditions such that the endothelial cells form a confluent layer of cells on the epithelial side of the membrane; and placing alveolar epithelial cells into the upper chamber of the vessel under conditions such that the endothelial cells migrate through the pores in the membrane and attach to the endothelial side of the membrane to form a confluent layer of the endothelial cells on the endothelial side of the membrane in the lower chamber and the alveolar epithelial cells form a confluent layer of the alveolar epithelial cells on the epithelial side of the membrane in the upper chamber.

The present invention further provides a method for determining the transport rate of pathogens through an artificial organ system comprising placing pathogens in contact with the epithelial cell layer of the artificial organ system of the present invention under conditions such that the pathogens enter or pass through or between the epithelial cells and migrate through the membrane and into or through or between the endothelial cells; and determining the number of pathogens present on the endothelial side of the membrane, the number of pathogens providing a measure of the transport rate of the pathogens through an artificial organ system.

Also provided is a method for determining the transport rate of pulmonary pathogens through an artificial lung system comprising placing pulmonary pathogens in contact with the alveolar epithelial cell layer of the artificial lung system of the present invention under conditions such that the pulmonary pathogens enter or pass through or between the alveolar epithelial cells and migrate through the membrane and into or through or between the endothelial cells; and determining the number of pulmonary pathogens present on the endothelial side of the membrane, the number of pulmonary pathogens providing a measure of the transport rate of the pulmonary pathogens through an artificial lung system.

The present invention further provides a method for determining transport mechanisms of pathogens through an artificial organ system comprising placing pathogens in contact with the epithelial cell layer of the artificial organ system of the present invention under conditions such that the pathogens enter or pass through or between the epithelial cells and migrate through the membrane and into or through or between the endothelial cells; processing the artificial organ system for examination of the presence of the pathogens within the artificial organ system with a microscope; and observing the pathogens within the artificial organ system in a microscope in order to determine the characteristics of the transport mechanisms of the pathogens.

Also provided is a method for determining transport mechanisms of pulmonary pathogens through an artificial lung system comprising placing pulmonary pathogens in contact with the alveolar epithelial cell layer of the artificial lung system of the present invention under conditions such that the pulmonary pathogens enter or pass through or between the alveolar epithelial cells and migrate through the membrane and into or through or between the endothelial cells; processing the artificial lung system for examination of the presence of the pulmonary pathogens within the artificial lung system with a microscope; and observing the pulmonary pathogens within the artificial lung system in a microscope in order to determine the characteristics of the transport mechanisms of the pulmonary pathogens.

The present invention also provides a method for determining the transport rate of chemical substances through an artificial organ system comprising placing a chemical substance in contact with the epithelial cell layer of the artificial organ system of the present invention under conditions such that the chemical substance enters or passes through or between the epithelial cells, passes through the membrane and into or through or between the endothelial cells; and determining the amount of the chemical substance present on the endothelial side of the membrane, the amount of chemical substance providing a measure of the transport rate of the chemical substance through the artificial organ system.

Additionally, the present invention provides a method for determining the transport rate of chemical substances through an artificial lung system comprising placing a chemical substance in contact with the alveolar epithelial cell layer of the artificial lung system of the present invention under conditions such that the chemical substance enters or passes through or between the alveolar epithelial cells, passes through the membrane and into or through or between the endothelial cells; and determining the amount of the chemical substance present on the endothelial side of the membrane, the amount of chemical substance providing a measure of the transport rate of the chemical substance through the artificial lung system.

Also provided is a method for determining transport mechanisms of chemical substances through an artificial organ system comprising placing a chemical substance in contact with the epithelial cell layer of the artificial organ system of the present invention under conditions such that the chemical substance enters or passes through or between the epithelial cells and passes through the membrane and into or through or between the endothelial cells; processing the artificial organ system for examination of the presence of the chemical substance within the artificial organ system with a microscope; and observing the chemical substance within the artificial organ system in a microscope in order to determine the characteristics of the transport mechanisms of the chemical substance.

Further provided is a method for determining transport mechanisms of chemical substances through an artificial lung system comprising placing a chemical substance in contact with the alveolar epithelial cell layer of the artificial lung system of the present invention under conditions such that the chemical substance enters or passes through or between the alveolar epithelial cells and passes through the membrane and into or through or between the endothelial cells; processing the artificial lung system for examination of the presence of the chemical substance within the artificial lung system with a microscope; and observing the chemical substance within the artificial lung system in a microscope in order to determine the characteristics of the transport mechanisms of the chemical substance.

DESCRIPTION OF THE PREFERRED EMBODIMENTS

The present invention may be understood more readily by reference to the following detailed description of specific embodiments and the Examples included herein.

The present invention provides an artificial organ system comprising an endothelial cell layer, an epithelial cell layer and an artificial microporous membrane, having pores therein, disposed between and in direct contact with the endothelial cell layer and the epithelial cell layer such that the membrane has an endothelial side and an epithelial side. The present invention also provides an artificial organ system contained in a vessel comprising an upper chamber containing the epithelial cells and a lower chamber containing the endothelial cells. By being in direct contact with the artificial microporous membrane, the endothelial cell layer and the epithelial cell layer are separated by a distance no greater than the thickness of the membrane, which can range from 10 to 200 microns.

The present invention also provides an artificial lung system comprising an endothelial cell layer, an alveolar epithelial cell layer and an artificial microporous membrane, having pores therein, disposed between and in direct contact with the endothelial cell layer and the alveolar epithelial cell layer such that the membrane has an endothelial side and an epithelial side. The present invention also provides an artificial lung system contained in a vessel comprising an upper chamber containing the epithelial cells and a lower chamber containing the endothelial cells. By being in direct contact with the artificial microporous membrane, the endothelial cell layer and the alveolar epithelial cell layer are separated by a distance no greater than the thickness of the membrane, which can range from 10 to 200 microns.

As used herein, "vessel" means any of a variety of well known containers for tissue cultures. For example, such vessels can be in the form of vials, bottles, tubes, chambers, flasks, or tissue culture wells present as either single well tissue culture plates or multiple well tissue culture plates of glass, metal or plastic, among others.

As used herein, "endothelial cell" means a human or other (e.g. bovine) cell which lines the blood and lymphatic vessels and various other body cavities (6). Human endothelial cells are preferred because they are more relevant for the study of human disease and chemical transport in humans. Human endothelial cells can include the human microvascular endothelial cell line, HMEC-1 (ATCC No. CRL 10636), the human liver endothelial cell line, HLEC (available from the Centers for Disease Control and Prevention, Atlanta, Ga.) and the human umbilical cord cell line, HUV-EC-C (ATCC No. CRL 1730), as well as primary endothelial cell cultures, among others. The endothelial cells of the artificial lung system can be of the human lung endothelial cell line, HULEC (available from the Centers for Disease Control and Prevention, Atlanta, Ga.), among others. Numerous non-human endothelial cells are publicly available and can be used to study various pathogens, particularly non-human pathogens.

As used herein, "epithelial cell" means a human or other cell which forms the outer surface of the body and lines organs, cavities and mucosal surfaces (6). For example, such epithelial cells can comprise the human endometrial carcinoma cell line, HecIB (ATCC No. HTB 112), the human cervical carcinoma cell line, HeLa (ATCC No. CCL 2), the human lung carcinoma cell line, A549 (ATCC No. CCL 185) and the human larynx carcinoma cell line, Hep2 (ATCC No. CCL 23), as well as primary epithelial cell cultures, among others. Numerous non-human epithelial cells are publicly available and can be used to study various pathogens, particularly non-human pathogens. As used herein, "layers" means confluent sheets of cells having a thickness of one cell or several cells.

As used herein, an "alveolar epithelial cell" means a human or other cell which forms the outer surface of the alveolar sacs in the lungs. For example, such alveolar epithelial cells can comprise primary lung pneumocytes, the human lung carcinoma cell line, A549 (ATCC No. CCL 185), the human larynx carcinoma cell line Hep2 (ATCC No. CCL 23), and the human lung carcinoma cell lines A427 (ATCC No. HTB 53), Calu-1 (ATCC No. HTB 54), Calu-3 (ATCC No. HTB 55) Calu-6 (ATCC No. HTB 56) ChaGo K1 (ATCC No. 168), NCI-H446 (ATCC No. HTB 171), NCI-H460 (ATCC No. 177), NCI-H520 (ATCC No. 182), NCI-H596 (ATCC No. 178), NCI-H661 (ATCC No. 183), SK-LU-1 (ATCC No. HTB 57), SK-MES-1 (ATCC No. HTB 58), SW900 (ATCC No. HTB 59), as well as other primary alveolar epithelial cell cultures, among others. Numerous non-human alveolar epithelial cells are publicly available and can be used to study various pulmonary pathogens, particularly non-human pathogens.

As used herein, "basal surface" means that side of the membrane which faces the bottom of the vessel and is, thus, oriented downward. Also as used herein, "apical surface" means that side of the membrane facing away from the bottom of the vessel and is, thus, facing upward. In the completed artificial organ system, the apical surface and the epithelial side will coincide and the basal surface and the endothelial side will coincide.

As used herein, "endothelial side" means the surface of the membrane upon which the endothelial cell layer is growing. When the artificial organ system is contained in a vessel having an upper chamber and a lower chamber, the endothelial side or basal surface of the membrane faces into the lower chamber. As used herein, "epithelial side" is the surface of the membrane upon which the epithelial cell layer is growing. When the artificial organ system is contained in a vessel having an upper chamber and a lower chamber, the epithelial side or apical surface of the membrane faces into the upper chamber.

As used herein, an "artificial microporous membrane" means a membrane having a thickness of between 10 and 200 microns, with a preferable thickness range between 15 and 30 microns and pores within the membrane of substantially uniform size and ranging in diameter from 0.45 microns to 10 microns, most preferably having a diameter of 3 microns. The membrane can comprise in whole or in part a synthetic (i.e., not naturally occurring) material, or it can comprise a naturally occurring material in a molecular or ultrastructural arrangement not normally found in nature. The membrane can be composed of a biactually stretched fluoropolymer or any material suitable for generating a track etch capillary pore membrane. For example, the membrane can be composed of polycarbonate, polytetrafluoroethylene, polyester, nitrocellulose, cellulose acetate, polycarbonate or polystyrene, among others. The membrane can also be coated on one or both sides with a biocompatible material to facilitate attachment of cells to the membrane surfaces. This biocompatible material can consist of collagen, laminin, proteoglycan, vitronectin, fibronectin, poly-D-lysine or polysaccharides, among others, such as are available, for example, from Biocoat Cell Environments, Collaborative Biomedical Products, Becton Dickinson, Bedford, Mass. These materials can also form the basement membrane-like layer described below.

The membrane can be supported a distance from the bottom of the vessel by any of the well known means. The membrane can be supported by a supporting means, for example a plastic frame, such that the membrane can be suspended in a vessel such as a tissue culture well and such that the plastic frame forms a chamber around the membrane into which fluids can be placed. For example, the membrane can be built into a Transwell-COL™ insert (Costar, Cambridge, Mass.). Alternative supporting means can include wire baskets or supports made from gels, among others. The membrane can be supported above the bottom of the vessel at any distance from the bottom as long as the membrane can be covered by a fluid medium within the vessel and a sufficient amount of space exists between the endothelial cell layer and the bottom of the vessel to allow nutrients in the fluid medium to contact the endothelial cell layer. Other biocompatible support means either known or subsequently developed can be used to support the membrane.

Also provided is a method of constructing an artificial organ system, comprising the steps of placing an artificial microporous membrane, having pores therein, into a vessel and supporting the membrane a distance from the bottom of the vessel to create an upper and lower chamber in the vessel such that the membrane has an endothelial side facing into the lower chamber of the vessel and an opposite epithelial side facing into the upper chamber of the vessel; placing endothelial cells into the upper chamber of the vessel under conditions such that the endothelial cells form a confluent layer of cells on the epithelial side of the membrane; and placing epithelial cells into the upper chamber of the vessel under conditions such that the endothelial cells migrate through the pores in the membrane and attach to the endothelial side of the membrane to form a confluent layer of the endothelial cells on the endothelial side of the membrane in the lower chamber and the epithelial cells form a confluent layer of the epithelial cells on the epithelial side of the membrane in the upper chamber.

A method is also provided for constructing an artificial lung system, comprising the steps of placing an artificial microporous membrane, having pores therein, into a vessel and supporting the membrane a distance from the bottom of the vessel to create an upper and lower chamber in the vessel such that the membrane has an endothelial side facing into the lower chamber of the vessel and an opposite epithelial side facing into the upper chamber of the vessel; placing endothelial cells into the upper chamber of the vessel under conditions such that the endothelial cells form a confluent layer of cells on the epithelial side of the membrane; and placing alveolar epithelial cells into the upper chamber of the vessel under conditions such that the endothelial cells migrate through the pores in the membrane and attach to the endothelial side of the membrane to form a confluent layer of the endothelial cells on the endothelial side of the membrane in the lower chamber and the alveolar epithelial cells form a confluent layer of the alveolar epithelial cells on the epithelial side of the membrane in the upper chamber.

The conditions under which the endothelial cells form a confluent layer of cells on the epithelial side of the membrane can, for example, comprise maintaining the endothelial cells and artificial microporous membrane in endothelial basal medium with about 7.0% fetal bovine serum at about 37° C. in about 5.0% carbon dioxide for about eight days. Other physiologically balanced medium can be used, providing it contains adequate growth factors for endothelial cells. The medium can contain from 0 to 20% fetal bovine serum. The cells can be incubated at temperatures ranging from 25° C. to 42° C. and in a concentration of carbon dioxide ranging from 2% to 8%. The endothelial cells can be cultured for six to ten days prior to the addition of the epithelial cells.

The conditions under which the endothelial cells migrate through the pores in the membrane and attach to the endothelial side of the membrane to form a confluent layer of the endothelial cells on the endothelial side of the membrane, in the lower chamber and the epithelial cells form a confluent layer of the epithelial cells on the epithelial side of the membrane, in the upper chamber can, for example, comprise maintaining the endothelial cells and epithelial cells in endothelial basal medium with about 7.0% fetal bovine serum at about 37° C. in about 5.0% carbon dioxide for 15–20 days. Other physiologically balanced medium can be used, providing it contains adequate growth factors for endothelial cells and epithelial cells (e.g. Eagle's minimum essential medium). The medium can contain from 0 to 20% fetal bovine serum. The cells can be incubated at temperatures ranging from 25° C. to 42° C. and in a concentration of carbon dioxide ranging from 2% to 8%. Upon establishment of the artificial lung system, the epithelial cells and endothelial cells can be cultured for about four weeks.

The artificial organ system can further include a layer of basement membrane material (biocompatible material) in contact with the artificial microporous membrane. Specifically, the artificial lung system can comprise a layer of basement membrane material in direct contact with the epithelial side of the membrane and with the alveolar epithelial cell layer. As used herein, "basement membrane material" means a porous extracellular matrix which functions as a support structure for the cell layers of the artificial organ system which functions in a manner similar to the way basement membrane material functions as a support structure in whole organs. This basement membrane material is included during construction of the artificial organ system and is placed in direct contact with the apical surface of the membrane prior to addition of the endothelial cells. The endothelial cells then establish a confluent monolayer on the surface of the basement membrane material and subsequently migrate through both the basement membrane material and membrane to the basal surface of the membrane upon addition of the epithelial cells to the apical surface. Thus, the basement membrane material coats the membrane but does not block the migration of endothelial cells, pathogens or other chemical substances through the pores of the membrane.

The biocompatible materials described herein can form the present basement membrane. The basement membrane material can include, but is not limited to, an extracellular matrix composed of laminin and collagen (e.g., Matrigel®, available from Collaborative Biomedical Products, Becton Dickinson, Bedford, Mass.) or any other cellular matrix material comprising laminin, collagen, fibronectin or any combination of these, among others. These cellular matrix materials are suitable for almost every type of artificial organ system. However, certain systems may require optimization studies to identify the best matrix material to include in a particular type of artificial organ system. The artificial organ system and the artificial lung system in particular can be used as a study model to evaluate the effects of various extracellular matrix materials on the integrity of the cell layers, the ability of pathogens and chemical substances to pass through the system as well as the effects of various extracellular matrix materials on the mechanisms of transport of pathogens and chemical substances through the system.

In the artificial lung system, alveolar macrophages can be present in the upper chamber and can either be suspended in liquid medium above the alveolar epithelial cell layer or in contact with the alveolar epithelial cells of the alveolar epithelial cell layer. The presence of alveolar macrophages on the epithelial side of the membrane more closely mimics the in vivo environment within the lung, in which alveolar macrophages are present within the alveolar sacs. Thus, the construction of the artificial lung system can include placing alveolar macrophages in the upper chamber containing the alveolar epithelial cells after establishment of the artificial lung system. The alveolar macrophages can be obtained from the alveolar fluid obtained by alveolar lavage. For example, a tube can be placed into the lung and the alveoli can be sprayed with sterile saline which can then be suctioned from the lung as alveolar lavage fluid. The alveolar macrophages can be separated from other cells and particulate materials in the alveolar lavage fluid by techniques for separation of macrophages that are standard in the art (e.g., adherence of macrophages to plastic surfaces). Similarly, macrophages normally present in the epithelia of other organs can be added to the artificial organ system of the present invention which is designed for study of those particular organs.

Also for the purpose of more closely mimicking the in vivo environment of the alveolar sacs, the construction of the artificial lung system can also include placing alveolar fluid into the upper chamber after establishment of the artificial lung system. The alveolar fluid, obtained by using alveolar lavage protocols standard in the art, is a highly viscous solution comprising secreted surfactants, saline and other serum proteins. In other artificial organ systems, appropriate fluids can also be added to more closely represent the in vivo environment of other organs of interest.

In the artificial lung system or other artificial organ system, white blood cells (e.g., peripheral blood mononuclear cells (PBMC)) can be present in the lower chamber, either suspended in liquid medium around the endothelial cell layer or in contact with the endothelial cells of the endothelial cell layer. Both the rate and mechanisms of movement of the PBMC upward through the artificial lung system in response to the presence of pathogens or various chemical substances on the epithelial side of the artificial lung system can then be studied, as well as the effect the PBMC have on the infection process of various pathogens. This system can be used to study the movement and effects of immune cells in response to infection or other stimulus.

In addition, the production of various cytokines and chemokines within the artificial organ system can be studied. More specifically, cytokines and chemokines from the white blood cells or the alveolar epithelial and endothelial cells of the artificial lung system in response to various stimuli such as pathogenic organisms, toxins or other chemical compounds can be studied by assaying for the presence of the cytokines or chemokines of interest in the medium of the upper and/or lower chambers. Such assays can be carried out for example, by employing ELISA protocols, such as the one described in the Example section herein, in which monoclonal antibodies specific for certain cytokines or chemokines are used for detection of the presence of these substances in a fluid substrate. Chemical compounds and toxins which can be introduced to the artificial lung system can include but are not limited to tar, nicotine, coal dust, asbestos, oxygen radicals and the like. These chemical compounds can be introduced into the artificial lung system on either the epithelial or endothelial side, depending on where a given substance would be known to interact with lung tissue in the body. For example, the affects of toxic oxygen radicals, which would enter the alveolar sacs through inhalation, can be studied by introducing these molecules into the artificial lung system on the epithelial side of the membrane. Alternatively, the affects of nitrous oxide, which is produced by white blood cells, can be studied by introducing this compound on both the epithelial and endothelial sides of the membrane. An example of a substance whose affects would be studied by being added to the endothelial side of the membrane is red blood cells, which would be present in the in vivo environment in blood vessels lined with endothelial cells. Therefore, construction of the artificial lung system can further include placing white blood cells in the lower chamber containing the endothelial cells, after establishment of the artificial lung system. These cells can be obtained by methods well known in the art and as described, for example in the Example section herein.

Because the epithelial cells lining the alveolar sacs of the lungs are not normally submerged in fluid in a healthy physiological state, to provide an even more physiologically accurate model of the in vivo environment of the lung, the upper chamber can contain no or a minimal amount of fluid medium and the humidity in the upper chamber can be maintained at a level which keeps the epithelial cells healthy and/or mimics the internal environment of the alveolar sac. Pathogens and other chemical substances in solid, liquid or gaseous state can be introduced into the upper chamber and the affects of these agents on the artificial lung system under these conditions can be determined.

The artificial organ system or artificial lung system can also be constructed by placing an artificial microporous membrane, having pores therein, into a vessel such that a first surface of the membrane is facing upward; placing endothelial cells into the vessel under conditions such that the endothelial cells form a confluent layer of cells on this upward-facing first surface of the membrane; inverting the membrane in the vessel and supporting the membrane a distance from the bottom of the vessel to create an upper and lower chamber in the vessel such that the first surface containing the endothelial cells is now facing downward into the lower chamber of the vessel and the opposite second surface is facing upward into the upper chamber of the vessel. Epithelial cells, either alveolar or otherwise, can be placed into the upper chamber of the vessel under such conditions that the epithelial cells form a confluent layer of cells on the upward facing second surface of the membrane.

The construction of the artificial organ system or artificial lung system can further include placing a means for maintaining movement of fluid medium in the lower chamber after establishment of the artificial lung system. Such means can include, but is not limited to, a magnetic stir bar and a flow chamber, among others. For example, a magnetic stir bar can be placed on the bottom of the lower chamber of the vessel and the vessel can be placed on a magnetic stir plate to provide movement of liquid medium within the lower chamber. Similarly, a system for the movement of liquid medium through the lower chamber of the vessel can be established by methods well known in the art. The movement of fluid in or through the lower chamber of the artificial organ system mimics the movement of blood through the blood vessels and thus, the effects of substances which can be present in the blood can be studied by introducing these substances into the artificial organ system by placing them into the medium which is moving in or through the lower chamber. For example, red blood cells which have abnormal shapes, such as sickled red blood cells, can be added to the system to study the interactions of these cells with the cell layers of the artificial organ system.

The present invention further provides a method for determining the transport rate of pathogens through an artificial organ system comprising the steps of placing pathogens in contact with the epithelial cell layer of the artificial organ system of the present invention under conditions such that the pathogens enter or pass through or between the epithelial cells and migrate through the membrane and into or through or between the endothelial cells; and determining the number of pathogens present on the endothelial side of the membrane, either in contact with the endothelial cells or in the liquid medium in the lower chamber, the number of pathogens providing a measure of the transport rate of the pathogens through an artificial organ system.

The present invention further provides a method for determining the transport rate of pulmonary pathogens through an artificial lung system comprising the steps of placing pulmonary pathogens in contact with the alveolar epithelial cell layer of the artificial lung system of the present invention under conditions such that the pulmonary pathogens enter or pass through or between the alveolar epithelial cells and migrate through the membrane and into or through or between the endothelial cells; and determining the number of pulmonary pathogens present on the endothelial side of the membrane, either in contact with the endothelial cells or in the liquid medium in the lower chamber, the number of pulmonary pathogens providing a measure of the transport rate of the pulmonary pathogens through an artificial lung system.

As used herein, "pulmonary pathogen" means an organism that causes a disease state or pathological syndrome in the lungs or that can spread to other organs and internal body regions via the lungs. Examples of such pulmonary pathogens include but are not limited to *Mycobacterizim tuberculosis, Mycoplasma pneumoniae, Streptococcus pneumoniae, Histoplasma capsulatum, Legionella pneumophila* and respiratory viruses such as, for example, influenza, rhinovirus and Hantavirus, among others, as well as any other pathogen that can infect the lungs or through the lungs.

Also provided is a method for determining transport mechanisms of pathogens through an artificial organ system comprising the steps of placing the pathogens in contact with the epithelial cell layer of the artificial organ system of the present invention under conditions such that the pathogens enter or pass through or between the epithelial cells and migrate through the membrane and into or through or between the endothelial cells; processing the artificial organ system for examination of the presence of the pathogens within the artificial organ system with a microscope; and observing the pathogens within the artificial organ system in a microscope in order to determine the characteristics of the transport mechanisms of the pathogens.

Also provided is a method for determining transport mechanisms of pulmonary pathogens through an artificial lung system comprising the steps of placing the pulmonary pathogens in contact with the alveolar epithelial cell layer of the artificial lung system of the present invention under conditions such that the pulmonary pathogens enter or pass through or between the alveolar epithelial cells and migrate through the membrane and into or through or between the endothelial cells; processing the artificial lung system for examination of the presence of the pulmonary pathogens within the artificial lung system with a microscope; and observing the pulmonary pathogens within the artificial lung system in a microscope in order to determine the characteristics of the transport mechanisms of the pulmonary pathogens.

An additional asset of this artificial organ system is its potential adaptability for the study of a wide variety of organisms. Several epithelial cell lines have been used in this system, including Chang conjunctival cells, which have been used to show differences between a virulent and an avirulent strain of *Haemophilus influenzae* biogroup aegyptius. For any organism to be examined, it is routine to construct an artificial organ system, as described herein, using physiologically relevant epithelial and endothelial cell lines. The endothelial layer can be a different vascular line, such as human umbilical vein cells, perhaps more relevant to the pathogenesis of a given organism. Immunological factors (e.g. antibodies or phagocytic cells) can be introduced into the system to examine the infectious process in an environment even more closely resembling what the organism encounters in vivo.

The present invention also provides a method for determining the transport rate of chemical substances through an artificial organ system comprising the steps of placing a chemical substance in contact with the epithelial cell layer of the artificial organ system of the present invention under conditions such that the chemical substance enters or passes through or between the epithelial cells, passes through the membrane and into or through or between the endothelial cells; and determining the amount of the chemical substance present on the endothelial side of the membrane, either in contact with the endothelial cells or in the liquid medium in the lower chamber, the amount of chemical substance providing a measure of the transport rate of the chemical substance through the artificial organ system.

The present invention also provides a method for determining the transport rate of chemical substances through an artificial lung system comprising the steps of placing a chemical substance in contact with the alveolar epithelial cell layer of the artificial lung system of the present invention under conditions such that the chemical substance enters or passes through or between the alveolar epithelial cells, passes through the membrane and into or through or between the endothelial cells; and determining the amount of the chemical substance present on the endothelial side of the membrane, either in contact with the endothelial cells or in the liquid medium in the lower chamber, the amount of chemical substance providing a measure of the transport rate of the chemical substance through the artificial lung system.

Also provided is a method for determining transport mechanisms of chemical substances through an artificial organ system comprising the steps of placing a chemical substance in contact with the epithelial cell layer of the artificial organ system of the present invention under conditions such that the chemical substance enters or passes through or between the epithelial cells and passes through the membrane and into or through or between the endothelial cells; processing the artificial organ system for examination of the presence of the chemical substance within the artificial organ system with a microscope; and observing the chemical substance within the artificial organ system in a microscope in order to determine the characteristics of the transport mechanisms of the chemical substance.

Also provided is a method for determining transport mechanisms of chemical substances through an artificial lung system comprising the steps of placing a chemical substance in contact with the alveolar epithelial cell layer of the artificial lung system of the present invention under conditions such that the chemical substance enters or passes through or between the alveolar epithelial cells and passes through the membrane and into or through or between the endothelial cells; processing the artificial lung system for examination of the presence of the chemical substance within the artificial lung system with a microscope; and observing the chemical substance within the artificial lung system in a microscope in order to determine the characteristics of the transport mechanisms of the chemical substance.

The artificial organ system is a useful way to screen chemicals (e.g., drugs, medicaments or chemical toxins) to determine the movement of these substances through the artificial organ system. Such studies can also provide useful information on the effectiveness of applications such as drug treatments and vaccines whose mechanism of action involves blocking the binding of certain pathogens to host cells. In the artificial lung system, such chemicals can be, for example, antibiotics, antiviral drugs, or drugs to treat lung diseases such as cystic fibrosis, asbestosis, etc., as well as vaccine and lytic peptide therapeutics against lung and upper respiratory pathogens, among others.

The chemicals of interest can be detected on the endothelial side of the membrane, either in contact with the endothelial cells or in the liquid medium in the lower chamber, or within the artificial organ system by methods well known to those of ordinary skill in the art. For example, immunofluorescent and immunohistochemical reagents can be applied to the cells of the artificial organ system to identify and localize the presence of various substances added to the artificial organ system.

Chemicals can be detected in the medium by protocols standard in the art for identifying the presence of a substance in a liquid substrate. For example, the liquid medium can be centrifuged to pellet any solid materials, which can then be detected by immunoassay. Alternatively, substances of interest can be precipitated out of solution by salting out techniques or immunoprecipitation. Chemical substances of interest can also be identified by chromatography protocols, gel filtration methods and electrophoretic separation protocols, among others.

As used herein, "processing" means placing the samples of cells and membrane of the artificial organ system in the appropriate orientation into a tissue fixing reagent, embedding the samples in either paraffin or plastic, sectioning the samples and placing the sections on either glass slides or metal grids, staining the samples and observing the samples in either a light or electron microscope. The artificial organ system can be prepared for observation in a transmission electron microscope according to, for example, the protocol provided herein in the Examples section. The artificial organ system can also be prepared for histochemical and fluorescence microscopy, using protocols well known in the art.

The present invention is more particularly described in the following examples which are intended as illustrative only since numerous modifications and variations will be apparent to those skilled in the art.

EXAMPLES

Bacterial Strains

*Mycobacterium tuberculosis* Erdman, *Mycobacterium bovis* BCG (from the culture collection of the Tuberculosis and other Mycobacteriosis Branch, Division of AIDS, STD and TB Laboratory Research, National Center for Infectious Disease, CDC) and *Mycobacterium tuberculosis* strain #9, isolated from a patient with AIDS (provided by Dr. Robert Horsburgh, Atlanta, Ga.) were grown in Middlebrook 7H9 broth (Carr-Scarborough, Atlanta, Ga.) at 37° in 5% $CO_2$ with intermittent shaking for seven days. Broths were adjusted to an $OD_{600}$ of 0.5 (approximately $10^7$ colony forming units (cfu)/ml) and aliquots were frozen at −70° C. These stocks were used for all subsequent experimental infections.

Artificial Lung System Construction

A Transwell-COL™ insert (Costar, Cambridge, Mass.) with 3.0 μm pores was placed in each well of a six well tissue culture cluster plate. HULEC endothelial cells ($1\times10^5$ cells/ml) were suspended in endothelial basal medium (EBM) (Gibco, Grand Island, N.Y.) with 7% fetal bovine serum (FBS) and 3 ml aliquots were added to each upper chamber (above the membrane). EBM+7% FBS (without cells) was added to the lower chamber (beneath the Transwell insert) in sufficient quantity to completely cover the membrane. The cells were incubated at 37° C. in 5% $CO_2$ for 7–8 days allowing formation of a continuous monolayer. The medium was removed from both upper and lower chambers and a suspension of A549 human lung epithelial cells (ATCC#CCL185) ($1\times10^5$ cells/ml) in minimal essential medium (MEM) with 5% FBS was added to the upper chamber. Fresh EBM with 7% FBS was added to the lower chamber. At seven day intervals, all medium was removed from both chambers and replaced with fresh EBM with 7% FBS. As demonstrated by histological analysis, the artificial lung system was completely formed and ready for use 15–20 days after the addition of the epithelial cell layer.

Fluorescence microscopy was used to determine the orientation of the cell layers in relation to the membrane. All cells were stained with Bodipy 581\591 phalloidin (Molecular Probes, Inc., Eugene, Oreg.) which stained the F actin of both cell layers. The cells were then stained with antibodies to the epithelial membrane antigen (DAKO, Carpinteria, Calif.) labelled with fluorescein isothiocyanate.

Actin in all cells fluoresced red while the outer membrane of the epithelial cells fluoresced green.

When epithelial cells were added to the chambers after the endothelial monolayer was established on the top side of the membrane, the endothelial cells migrated through the 3 µm pores to the basal (endothelial) side of the membrane where they remained. The artificial membrane appeared to function as a basement membrane for both the epithelium and the endothelium. As the epithelial cells grew, this layer became several cells thick and, in some cases, the cells differentiated into a columnar or cuboidal form. Determination of artificial lung system integrity (confluency) was based on microscopic observation and on the minimal passage of inert uncharged beads through the artificial lung system. Approximately $10^7$ colored polystyrene beads, 0.833 µm in diameter, (Seradyn, Indianapolis, Ind.) were added to 1 ml of tissue culture medium in the upper chamber. After three hours, the medium in the lower chamber was removed and centrifuged. Less than 0.01% of beads were observed to have passed into the lower chamber, suggesting that no gaps as large as 0.833 µm existed in the cell layers.

Thus, an important feature of the invention is the modeling of cell-to-cell communication between and among epithelial and endothelial cells that occurs in vivo. Cellular communication occurs in the artificial organ system model as evidenced by the fact that when epithelial cells are added to the system after the endothelial monolayer is established on the apical side of the membrane, the endothelial cells migrate through the 3 µm pores to the basal side of the membrane where they re-establish a monolayer. The central membrane appears to function as a basement membrane for both the epithelium and the endothelium. In the artificial organ system, when a layer of basement membrane material is placed in direct contact with the epithelial side of the membrane, the basement membrane material can augment the function of the artificial microporous membrane as a basement membrane for the epithelial cell layer.

Artificial Lung System Infection

The inoculation of a vessel containing the artificial lung system with a pathogen allows for the study of a number of virulence characteristics of the pathogen, including attachment, invasion, transcytosis and exit or extracellular passage through tight junctions. One can also examine the effect of various inhibitors of bacterial or host cell function or of antibodies on each of these aspects of the infectious process. Thus, it is possible to study the effect of inhibitors of host cell microfilament and microtubule function, pinocytosis, and protein synthesis, and exactly how the inhibitors interfere with the infectious process.

Before infection of the artificial lung system, all medium was removed, the artificial lung system was washed once with phosphate-buffered saline (PBS), and EBM with 10% human serum was added (1 ml in the upper chamber, 1 ml in the lower chamber). Frozen aliquots of bacteria were thawed and centrifuged and each pellet was resuspended in 100 µl of EBM (approximately $10^7$ cfu), which was added to the upper chamber of each well. For each time point, two wells were infected with each strain. To one of these wells, peripheral blood mononuclear cells (PBMC) were added to the lower chamber. Plates were incubated at 37° C. in 5% $CO_2$ for 4, 24 or 48 hours. At each time point, all contents of the lower chamber were collected and centrifuged at 14,000 rpm to pellet the bacteria. Supernatants were removed and frozen at −70° C. for cytokine assays. Bacteria were suspended in 0.1% Triton X100 and dilutions were plated on Middlebrook 7H10 medium to determine numbers of organisms able to pass through the cell layer system.

Other methods of counting bacterial cells can also be used without any expected difficulty. Medium in the upper chamber was also removed and centrifuged and the supernatant frozen for cytokine analysis. The migration of the PBMC through the artificial lung system from the lower chamber to the upper chamber and the affect of the presence of the PBMC on migration rates of the various pathogens was also analyzed.

The artificial lung system was placed in 10% neutral buffered formalin for 4–12 hours and the artificial lung system was sectioned and processed for microscopic examination. Each artificial lung system was removed with forceps from the formalin and placed on its own 47 mm 0.2 µm Vericel™ (Gelman Sciences, Ann Arbor, Mich.) membrane. A sharp-pointed scalpel blade was used to cut the cell growth and its supporting Costar membrane away from the inside of the chamber, at the same time cutting all the way through the underlying Vericel membrane. The stack was then placed on another 47 mm Vericel membrane saturated with 70% alcohol. Supported by the larger Vericel membrane, the small stack of cell growth and artificial membranes was compactly rolled up with forceps. The original upper (apical/epithelial) side of the Costar membrane thus reliably corresponded to its concave surfaces once it was rolled up. Single-ply cotton string was used to tie off three areas near the center where cell growth was located. Transverse sections approximately 4 mm thick were cut from the middle of the roll between and on either side of the strings using a sharp blade and three sections were placed on edge on a square piece of wet lens paper. The lens paper was then folded over the membrane ensembles and the wrapped specimens were chemically processed as tissue, embedded to maximize exposure of the cell growth and the membrane. Cassettes were immersed in 70% ethanol for transfer. Specimens were processed for 16 hours in a Fisher Histomatic™ (Fisher Scientific, Pittsburgh, Pa.) tissue processor, embedded in Polyfin™ (Triangle Biomedical Sciences, Durham, N.C.) embedding medium (after removing strings) and sectioned at 4 µm on a Leitz 1512 microtome. Blocks were trimmed deeply enough to compensate for any retraction of the cell layer from the edges of the membranes. Sections were floated on a 40° C. water bath, collected on 3×1 inch glass microscope slides coated with aminosilane (A. Daigger and Co., Inc., Wheeling, Va.), warmed in a 60°–65° C. paraffin oven for 20–30 minutes and stained with acid fast stain.

Processing for Transmission Electron Microscopy (TEM)

Transwells were prepared for TEM by a modification of the procedure by the manufacturer (Costar Corporation, Cambridge, Mass.). Growth medium was removed and membranes were fixed with 2% glutaraldehyde for one hour at room temperature. Fixative was removed and replaced with collidine buffer. Specimens were either stored at 4° C. for later processing or immediately post-fixed with 1% osmium tetroxide for 45 minutes at 4° C. Osmium was removed and replaced with uranyl acetate. The specimens were held at 4° C. overnight and then dehydrated through a graded series of ethanol concentrations: 70% EtOH, 95% EtOH, 100% EtOH and 100% EtOH, each for ten minutes. Specimens were then infiltrated with complete embedding resin (LR White medium grade): 75% EtOH:25% resin for one hour, 50% EtOH:50% resin for one hour and 25%EtOH:75% resin for one hour. The wells were filled with complete resin and allowed to stand overnight (16 hours) at room temperature. Overnight resin was replaced with fresh resin and the dishes were placed in a 60° C. oven and allowed to polymerize for 72 hours. After polymerization, the plastic of the wells and sides of membrane inserts was removed and resin containing the filter was cut out and trimmed with a jeweler's saw. The embedded materials was sectioned with an ultramicrotome, placed on copper grids and stained with lead citrate and uranyl acetate for examination in the electron microscope.

Monolayer Preparation and Infection

HULEC lung endothelial cells suspended in EBM with 7% FBS or A549 human pneumocytes suspended in MEM with 5% FBS ($1\times10^5$ cells/ml) were added to T75 tissue culture flasks (Costar). Cells were incubated at 37° C. in 5% $CO_2$ until monolayers reached confluency. Prior to infection, culture medium was replaced with EBM with 10% human serum. Bacteria from frozen stock cultures were added to each well (approximately $10^7$ cfu/flask). After 4, 24, 48 or 72 hours of incubation, medium was removed and centrifuged to pellet bacteria. The supernatant was removed and frozen for cytokine analysis.

Isolation of Peripheral Blood Mononuclear Cells

Blood was collected in acid citrate dextrose anticoagulant. To sediment out the red blood cells, one ml of Gentran (6%) (Baxter Healthcare Corporation, Deerfield, Ill.), was added for each ten ml of blood. This was mixed gently and incubated at 37° C. for 30–60 minutes. The upper layer and some red cells were removed and washed with Hanks' balanced salt solution (HBSS) without calcium or magnesium and centrifuged for ten minutes at 1000×g. For each 50 ml of blood, the pellet was resuspended in HBSS to approximately ten ml and layered over five ml of Ficoll/Hypaque (Pharmacia Biotech, Uppsala, Sweden) in a 15 ml polypropylene tube. This gradient was centrifuged at 1000×g (2500 rpm in a table top centrifuge) for 30–45 minutes. The cells at the interface were collected with a Pasteur pipette and washed twice with three volumes of HBSS. After the final wash, the cells were resuspended in Iscoves Modified Dulbecco's Medium (IMDM) (Gibco BRL) with 10% pooled human male serum.

Cytokine and Chemokine Assays

Enzyme linked immunosorbent assays (ELISA) were performed to determine if infection of the cells of the artificial lung system resulted in the production of any of the following cytokines and chemokines: interleukin-8 (IL-8), Mip1-alpha, Mip1-beta and RANTES (7). The ELISAs were carried out according to the protocol provided in each of the Quantikine ELISA kits specific for each cytokine or chemokine of interest (R & D Systems, Minneapolis, Minn.), Each kit employs a sandwich ELISA technique whereby a monoclonal antibody specific for the cytokine or chemokine to be detected is coated onto the wells of a microtiter plate, which is provided in the kit. Samples of the medium from either the upper or lower chambers of the artificial lung system are added to the wells of the microtiter plate and the cytokine or chemokine, if present, is bound by the monoclonal antibody in the well. A second enzyme-linked polyclonal antibody is added to the well and binds to any cytokine or chemokine bound in the well. A substrate is added to produce a color reaction in the presence of bound second antibody if cytokine or chemokine is present and the amount of the cytokine or chemokine can be quantified by measuring the intensity of the color reaction spectrophotometrically. Commercial kits are available for detecting and quantitating most if not all known cytokines and chemokines.

Cytokine data from monolayers of A549 and HULEC cells show significantly higher production of interleukin-8, Mip1-alpha, Mip1-beta and RANTES by cells infected with M. tuberculosis Erdman as compared to cells infected with M. bovis BCG and uninfected controls. These cytokines are all monocyte chemoattractants known to be upregulated in the inflammatory response to infection. These monolayer results have been confirmed in cytokine assays in the artificial lung system. This phenomenon is expected to correlate with in vivo responses.

Enumeration of infected cells

Prepared sections of infected cells in the artificial lung system were examined by light microscopy. For each sample, 100 clearly defined cells were enumerated and the number of these cells infected with one or more bacteria was determined.

Primary Lung Pneumocyte Isolation and Culture

To isolate lung pneumocytes, the lung specimen is perfused via convenient airways with 0.15M saline and then with 20–40 ml. of 0.5% (w/v) bovine pancreatic trypsin (Sigma T-8003) in calcium and magnesium free balanced Hank's salt solution. The specimen is incubated at 37° C. for 30 minutes. Five ml of newborn calf serum and 15 ml of DNase I (500 µg/ml) is added and the lung is chopped into fine pieces. The pieces are transferred to a plastic flask with 20 ml of calcium and magnesium free balanced Hank's salt solution and the flask is shaken for five minutes at 37° C. The resulting cell suspension is then filtered through 125 µm and then through 30 µm nylon mesh. The cell suspension is then centrifuged at 400×g for ten minutes at 4° C. and the resulting pellet is resuspended in two ml of DMEM containing 10% newborn calf serum. This suspension is layered over a continuous Nycodenz density gradient prepared as follows: The Nycodenz solution is diluted with Tris-HCl buffer at ph 7.5 in ratios of 1:0, 3:1, 1:1 and 1:5. Two ml of each dilution is layered in the order of decreasing density. Two ml. of the cell suspension is then layered onto the gradient and the tube is then placed in a horizontal position and the gradient is allowed to diffuse for one hour at room temperature. The gradient is then centrifuged for 20 minutes at 1500×g at 4° C. The upper band, containing a mixture of pneumocytes and alveolar macrophages, is removed. The band is then washed two times by centrifugation in calcium and magnesium free balanced Hank's salt solution. The pellet is resuspended in DMEM with no serum added. The cells are plated onto three dishes of human IgG-coated plates prepared as follows: A volume of 3.6 ml of human IgG is suspended in 72 ml of TRIS buffer (pH 9.5) and six ml of this suspension is placed in a 100 mm bacteriological plastic dish. The dish is swirled completely cover the bottom surface and the dish is placed in a laminar flow hood at room temperature for three hours. The dish is then washed three times with sterile PBS and washed with DMEM just before the cells are added. The plates containing cells are placed in a 10% carbon dioxide incubator for one hour. The plates are tilted back and forth gently three times, exposing approximately three centimeters of the plate each time. The cell suspension is removed from the dish, pooled with other lung cell suspensions from other dishes and centrifuged at 400×g for eight minutes. The cells are resuspended in DMEM plus antibiotics and 10% fetal bovine serum.

Determination of Artificial Lung System Integrity

To determine integrity of the HULEC/membrane/A549 system, growth medium was removed and replaced with fresh EBM at one ml in the upper chamber and one ml in the lower chamber. Controls included one membrane without cells and one membrane with a confluent monolayer of Madin Darby canine kidney (MDCK) cells (ATCC CCL 34). One ml of 1% blue dextran 2000 (Pharmacia Biotech, Uppsala, Sweden) was added to each upper chamber and membranes were incubated for three hours. Contents of each lower chamber were removed and their optical densities determined.

There do not appear to be significant differences between *M. tuberculosis* Erdman and the clinical isolate, *M. tuberculosis* strain #9, in terms of their respective abilities to pass through the artificial lung system. However, passage numbers of both of these strains are consistently ten-fold higher than those of *M. bovis* BCG. These relationships remain the same when strains have been passed through human macrophages.

While the addition of PBMC to the lower chamber does not appear to significantly affect the migration of *M. tuberculosis* Erdman or *M. tuberculosis* strain #9 through the artificial lung system, the presence of PBMC does appear to inhibit the passage of *M. bovis*, with passage numbers decreasing from 50 to 75%.

Microscopic examination of the artificial organ system has revealed that mononuclear cells can be observed to migrate through the artificial organ system to the epithelial or apical surface in the upper chamber as early as four hours after infection, with increasing numbers of mononuclear cells seen in the upper chamber at later time points after infection.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties, as well as the references cited in these publications, are hereby incorporated by reference into this application in order to more fully describe the state of the art to which this invention pertains.

REFERENCES

1. Bloom, B. R., ed. 1994. Tuberculosis: Pathogenesis, Protection, and Control. ASM Press, Washington, D.C.
2. McDonough, K. A., Y. Kress, and B. R. Bloom. 1993. Pathogenesis of tuberculosis: interaction of *Mycobacterium tuberculosis* with macrophages. *Infect. Immun.* 61:2763-73.
3.. Bannenberg, A. M., Jr. 1982. Pathogenesis of pulmonary tuberculosis. *Am. Rev. Respir. Dis.* 125:25-29.
4. Mehta, P. K., C. H. King, E. H. White, J. J. Murtagh, Jr. and F. D. Quinn. 1996. Comparison of in vitro models for the study of *Mycobacterium tuberculosis* invasion and intracellular replication. *Infect. Immun.* 64:2673-79.
5. Graham, D. J., J. J. Alexander and M. Remedios. 1991. Aortic endothelial and smooth muscle cell co-culture: An in vitro model of the arterial wall. *Journal of Investigative Surgery* 4:487-494.
6. Taber's Cyclopedic Medical Dictionary, 12th Edition, F. A. Davis Co., Philadelphia, Pa.
7. Beu-Baruch, A., D. F. Michiel and J. J. Oppenheim. 1995. Signals and receptors involved in recruitment of inflammatory cells. *J. Biol. Chem.* 270:11703-11706.

What is claimed is:

1. An artificial lung system comprising an endothelial cell layer, an alveolar epithelial cell layer and an artificial microporous membrane, having pores therein, disposed between and in direct contact with the endothelial cell layer and the alveolar epithelial cell layer such that the membrane has an endothelial side and an epithelial side.

2. The artificial lung system of claim 1, wherein the system is contained in a vessel comprising an upper chamber, into which the epithelial side faces, and containing the alveolar epithelial cell layer and a lower chamber, into which the endothelial side faces, and containing the endothelial cell layer.

3. The artificial lung system of claim 1, wherein the endothelial cell layer consists of the cells of the human lung endothelial cell line, HULEC.

4. The artificial lung system of claim 1, wherein the alveolar epithelial cell layer consists of the cells of the human pneumocyte cell line, A549.

5. The artificial lung system of claim 1, wherein the alveolar epithelial cell layer consists of primary lung pneumocytes.

6. The artificial lung system of claim 1, wherein alveolar macrophages are present in the upper chamber.

7. The artificial lung system of claim 1, wherein the artificial microporous membrane comprises a membrane having pores of substantially uniform size and ranging in diameter from 0.45 microns to 10 microns.

8. The artificial lung system of claim 1, wherein a side of the artificial microporous membrane is a polycarbonate membrane.

9. The artificial lung system of claim 1, wherein a side of the membrane is coated with a biocompatible material which facilitates attachment of cells to the side.

10. The artificial lung system of claim 9, wherein the biocompatible material is selected from the group consisting of collagen, laminin, proteoglycan, vitronectin, fibronectin, poly-D-lysine and polysaccharide.

11. The artificial lung system of claim 9, wherein the biocompatible material forms a layer in direct contact with the epithelial side of the membrane and with the alveolar epithelial cell layer.

12. The artificial lung system of claim 11, wherein the biocompatible material is an extracellular matrix composed of laminin and collagen.

13. The artificial lung system of claim 1, wherein white blood cells are present in the lower chamber.

14. A method of constructing an artificial lung system, comprising:
  (a) placing endothelial cells into a vessel under cell culture conditions such that the endothelial cells form a confluent layer of cells on the epithelial side of an artificial porous membrane contained within the vessel, wherein the vessel has a bottom and the membrane, having pores therein, is supported a distance from the bottom of the vessel to create an upper chamber and a lower chamber such that the membrane has an endothelial side facing into the lower chamber of the vessel and an opposite epithelial side facing into the upper chamber of the vessel and wherein the endothelial cells are placed into the upper chamber of the vessel; and
  (b) placing alveolar epithelial cells into the upper chamber of the vessel under cell culture conditions such that the endothelial cells migrate through the pores in the membrane and attach to the endothelial side of the membrane to form a confluent layer of the endothelial cells on the endothelial side of the membrane in the lower chamber and the alveolar epithelial cells form a confluent layer of the alveolar epithelial cells on the epithelial side of the membrane in the upper chamber.

15. The method of claim 14, further comprising the step of placing alveolar fluid into the upper chamber of the vessel.

16. The method of claim 14, further comprising the step of placing a means for maintaining movement of liquid medium in the lower chamber in the vessel.

17. The method of claim 16, wherein the means for maintaining movement of liquid medium is a magnetic stir bar and the vessel is placed on a magnetic stir plate.

18. The method of claim 16, wherein the means for maintaining movement of liquid medium is a flow chamber.

19. The method of claim 14, further comprising the step of placing white blood cells in the lower chamber containing the endothelial cell layer.

20. The method of claim 14, further comprising the step of placing alveolar macrophages in the upper chamber containing the alveolar epithelial cell layer.

21. The method of claim 14, further comprising the step of placing a biocompatible basement membrane material in direct contact with the epithelial side of the membrane.

22. The method of claim 21, wherein the basement membrane material is an extracellular matrix composed of laminin and collagen.

23. The method of claim 14, wherein the conditions of step (b) comprise maintaining the endothelial cells in endothelial basal medium containing 7.0% fetal bovine serum at about 37° C. for about eight days.

24. The method of claim 14, wherein the conditions of step (b) comprise maintaining the alveolar epithelial cells and the endothelial cells concurrently in endothelial basal medium with about 7.0% fetal bovine serum at 37° in about 5.0% carbon dioxide for about 15 to 20 days.

* * * * *